United States Patent [19]

Asato et al.

[11] Patent Number: 4,877,888

[45] Date of Patent: Oct. 31, 1989

[54] 13-DEOXY-23-IMINO DERIVATIVES OF 13-DEOXY C-076-AGLYCONE COMPOUNDS

[75] Inventors: Goro Asato, Titusville; Donald J. France, Pennington, both of N.J.

[73] Assignee: American Cyanamid Company, Stamford, Conn.

[21] Appl. No.: 88,952

[22] Filed: Aug. 27, 1987

Related U.S. Application Data

[63] Continuation-in-part of Ser. No. 907,259, Sep. 12, 1986, abandoned.

[51] Int. Cl.⁴ ............................................. C07D 311/68
[52] U.S. Cl. ..................................................... 549/264
[58] Field of Search ........................ 549/264; 514/450

[56] References Cited

U.S. PATENT DOCUMENTS

| | | | |
|---|---|---|---|
| 4,171,314 | 10/1979 | Chabala et al. | 549/264 |
| 4,289,760 | 9/1981 | Mrozik et al. | 549/264 |
| 4,423,209 | 12/1983 | Mrozik | 549/264 |
| 4,427,663 | 1/1984 | Mrozik | 514/30 |
| 4,457,920 | 7/1984 | Mrozik | 549/264 |
| 4,547,520 | 10/1985 | Ide et al. | 549/264 |

OTHER PUBLICATIONS

Abstract of Japan 60/142991, Jul. 29, 1985.

*Primary Examiner*—Richard L. Raymond
*Assistant Examiner*—Ba K. Trinh
*Attorney, Agent, or Firm*—Estelle J. Tsevdos

[57] ABSTRACT

The present invention relates to novel 23-imino derivatives of C-076 wherein the C-076 compounds are not substituted at the 13-position. The C-076 compounds (collectively) are isolates from the fermentation broth of *Streptomyces avermitilis*. The precursor 23-oxo compounds are prepared by selectively oxidizing suitably protected 13-deoxy C-076 aglycone compounds by using oxidizing agents. Subsequently, the 23-oxo compounds are converted to the 23-imino compounds. These novel compounds have potent anthelmintic, insecticidal, ectoparasticidal, nematicidal and acaricidal activity. Compositions containing these 23-oxo and 23-imino derivatives of 13-deoxy C-076 aglycones also are described herein.

13 Claims, No Drawings

13-DEOXY-23-IMINO DERIVATIVES OF 13-DEOXY C-076-AGLYCONE COMPOUNDS

This application is a continuation-in-part of application, Ser. No. 907,259, filed Sept. 12, 1986, now abandoned.

BACKGROUND OF THE INVENTION

The present invention relates to new 23-oxo (keto) and 23-imino derivatives of the compounds collectively defined as 13-deoxy-C-076 aglycones. The C-076 antibiotics preferably are produced by the fermentation of the microorganism *Streptomyces avermitilis* with the 13-deoxy-C-076 aglycone compounds having been disclosed in U.S. Pat. No. 4,171,314, issued to Chabala et al on Oct. 16, 1979, incorporated herein by reference thereof.

The C-076 compounds are complex macrolides which have a 23-hydroxy substituent. The selective oxidation of this 23-hydroxy group to a 23-oxo group and the subsequent derivatization of the oxo group to afford 23-imino derivatives are the subject matter of the present invention. These 23-oxo and 23-imino derivatives of the 13-deoxy-C-076 aglycone compounds are useful for the prevention, treatment or control of helmintic, ectoparasitic, insect, acarid and nematode infections and infestations in warm-blooded animals and agricultural crops.

SUMMARY OF THE INVENTION

The present invention provides novel 23-oxo (keto) and 23-imino derivatives of the compounds designated 13-deoxy—C-076 aglycones.

The 13-deoxy-C-076 aglycone compounds have the following structural formula:

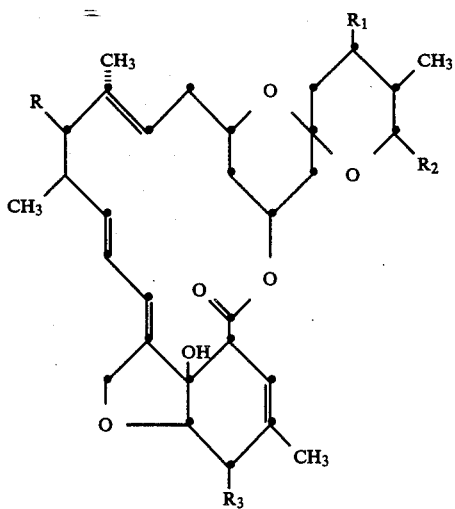

wherein the broken line indicates a single or a double bond; R is halogen or hydrogen; $R_1$ is hydroxy and is present only when said broken line indicates a single bond; $R_2$ is isopropyl or sec-butyl; and $R_3$ is methoxy or hydroxy.

The compounds of the present invention are useful anthelmintics, ectoparasiticides, insecticides, acaricides and nematicides in treating, preventing or controlling such diseases in warm-blooded animals, such as poultry, cattle, sheep, swine, rabbits, horses, dogs, cats and human beings.

Although these diseases have been recognized for years and therapies exist for the treatment and prevention of the diseases, the present invention provides novel compounds in the search for effective such therapy. For instance, U.S. application for Letters patent Ser. Nos. 907,186, 907,187, 907,188, 907,283, 907,281 and 907,284 of Asato and Asato et al, filed Sept. 12, 1986 and incorporated herein by reference thereto provide compounds for such treatments.

U.S. Pat. No. 3,950,360, Aoki et al, Apr. 13, 1976 discloses certain antibiotic substances obtained by culturing a Streptomyces microorganism, said compounds being useful as insecticides and acaricides. Further, an entire series of U.S. patents relates to certain compounds produced by the fermentation of *Streptomyces avermitilis* (U.S. Pat. No. 4,171,314, Chabala et al, Oct. 16, 1979; U.S. Pat. No. 4,199,569, Chabala et al, Apr.22, 1980; U.S. Pat. No. 4,206,205, Mrozik et al, June 3, 1980; U.S. Pat. No. 4,310,519, Albers-Schonberg, Jan. 12, 1982; U.S. Pat. No. 4,333,925, Buhs et al, June 8, 1982). U.S. Pat. No. 4,423,209, Mrozik, Dec. 27, 1983 relates to the process of converting some of these less desirable components to more preferred ones. Finally, British Patent Application No. 2166436 A discloses antibiotics also. European Patent Application Publication No. 170,006 also discloses useful such antibiotics.

The present compounds or the pharmaceutically and pharmacologically acceptable salts thereof exhibit excellent and effective treatment, prevention and/or control of these serious diseases of warm-blooded animals.

It is an object of the present invention, therefore, to provide novel 23-oxo and 23-imino derivatives of 13-deoxy-C-076 aglycone compounds. It is a further object to provide a process for the preparation of these derivatives and to provide methods for preventing, treating or controlling endo and ectoparasitic (collectively parasitic), insect, nematode, acarid and helmintic diseases and infestations in warm-blooded animals and agricultural crops by providing compositions containing prophylactically, therapeutically or pharmaceutically-effective amounts of the present novel compounds.

These and other objects of the invention will become apparent by the more detailed description of the invention provided hereinbelow.

DETAILED DESCRIPTION OF THE INVENTION

The 13-deoxy-C-076 aglycone compounds which may act as precursors of the present compounds are represented by the following structural formula,

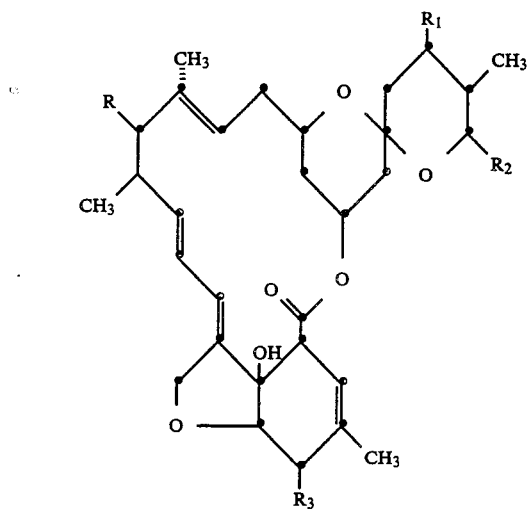

wherein the broken line indicates a single or a double bond; R is halogen or hydrogen; $R_1$ is hydroxy and is present only when said broken line indicates a single bond; $R_2$ is isopropyl or sec-butyl; and $R_3$ is methoxy or hydroxy.

The compounds of the instant invention are represented by the following structural formula:

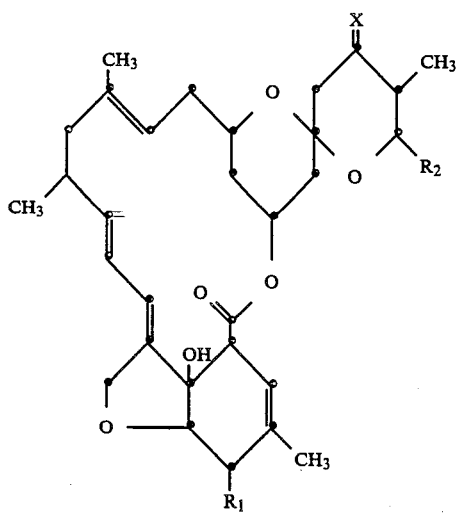

wherein $R_1$ is methoxy or hydroxy; $R_2$ is isopropyl or sec-butyl; X is oxygen, $NOR_4$, or $N-NHR_5$; $R_4$ is hydrogen, $C_1$–$C_6$ alkyl, $C_1$–$C_4$ alkoxymethyl, benzyl, allyl, propargyl, phenyl, $CH_2COO$-alkyl ($C_1$–$C_4$), N-($C_1$–$C_6$ alkyl)carbamoyl, N-(allyl)carbamoyl, N-(propargyl)-carbamoyl, N-(phenyl)carbamoyl, N-(chlorophenyl)-carbamoyl, N-(dichlorophenyl)carbamoyl, N-(benzyl)-carbamoyl, $C_1$–$C_6$ alkanoyl, chloroacetyl, methoxyacetyl, phenylacetyl, optionally substituted on the phenyl ring with one or two halogens, $C_1$–$C_4$ alkyl groups, $C_1$–$C_4$ alkoxy groups or nitro groups, phenoxyacetyl, optionally substituted on the phenyl ring by one or two halogens, $C_1$–$C_4$-alkyl groups, $C_1$–$C_4$ alkoxy groups or nitro groups, or benzoyl, optionally substituted with one or two halogens, $C_1$–$C_4$ alkyl groups, $C_1$–$C_4$ alkoxy groups or nitro groups; $R_5$ is

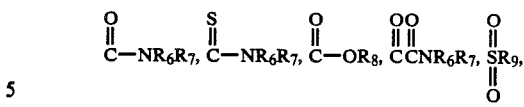

$C_1$–$C_6$ alkanoyl, formyl, $C_1$–$C_6$ alkyl,

benzoyl, optionally substituted with one or two halogens, $C_1$–$C_4$ alkyl groups, $C_1$–$C_4$ alkoxy groups or nitro groups; $R_6$ and $R_7$ are hydrogen or $C_1$–$C_6$ alkyl; or phenyl, optionally substituted with one or two halogens, $C_1$–$C_4$ alkyl, $C_1$–$C_4$ alkoxy, or phenyl optionally substituted with one or two halogens, $C_1$–$C_4$ alkyl groups, $C_1$–$C_4$ alkoxy groups or nitro groups, $R_8$ is $C_1$–$C_6$ alkyl or phenyl optionally substituted with one or two halogens, $C_1$–$C_4$ alkyl groups, $C_1$–$C_4$ alkoxy groups or nitro groups; $R_9$ is $C_1$–$C_6$ alkyl or phenyl optionally substituted with one or two halogens, $C_1$–$C_4$ alkyl groups, $C_1$–$C_4$ alkoxy groups or nitro groups; and the pharmaceutically and pharmacologically acceptable salts thereof.

A preferred group of compounds of structure (I) includes $R_1$ as hydroxy; $R_2$ as isopropyl or sec-butyl; X as oxygen, $NOR_4$,

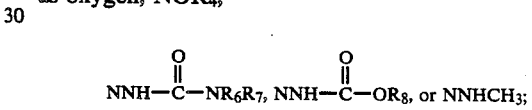

and $R_4$, $R_6$, $R_7$ and $R_8$ as described hereinabove.

Another preferred group of compounds of structure (I) includes $R_1$ as hydroxy; $R_2$ as isopropyl or sec-butyl; X as oxygen, $NOR_4$,

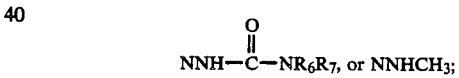

$R_4$ as $C_1$–$C_3$ alkyl, N-($C_1$–$C_4$ alkyl)carbamoyl, N-(phenyl)carbamoyl, N-(allyl)carbamoyl, N-(4-chlorophenyl)carbamoyl, N-(benzyl)carbamoyl, $C_1$–$C_4$ alkanoyl, chloroacetyl, methoxyacetyl, phenoxyacetyl, benzoyl and chlorobenzoyl; and $R_6$ and $R_7$ as described hereinabove.

The most preferred group of compounds of structure (I) includes $R_1$ as hydroxy; $R_2$ as isopropyl or sec-butyl; X as $NOR_4$,

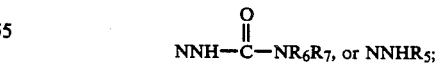

$R_6$ and $R_7$ as hydrogen or $C_1$–$C_4$ alkyl; and $R_5$ as $C_1$–$C_4$ alkyl or $C_1$–$C_4$ alkanoyl.

In preparing the compounds of the present invention, the 5-hydroxyl group must be protected. Suitable protecting groups are tri-substituted silyl groups, such as t-butyldimethylsilyl and trimethylsilyl, or trisubstituted silyloxyacetyl groups, such as t-butyldimethylsilyloxy acetyl group. The protecting groups, however, are not limited to these groups since other useful protecting groups such as acyl and substituted acyl, such as acetyl, trifluoroacetyl, chloroacetyl, trichloroacetyl, phenoxyacetyl and the like, are also useful in the present process.

One of the preferred protecting groups is t-butyldimethylsilyl. This group is attached to the 5-hydroxyl group by reacting an unprotected 5-hydroxy F-28249 compound with -butyldimethylsilyl chloride in the presence of a base, such as imidazole, pyridine, 4-dimethylaminopyridine, triethylamine and the like, in an aprotic solvent such as methylene chloride, toluene, ethylacetate, tetrahydrofuran, ethylenedichloride and the like. The reaction is stirred at a temperature of about 0° C. to 30° C., and the reaction is complete in several hours, depending on the temperature of the reaction. The completion of the reaction is usually monitored by high performance liquid chromatography (HPLC) using reverse phase on a Whatman Partisil CCS/$C_8$ rapid analysis column.

Another preferred protecting group is t-butyldimethylsilyloxy acetyl group. This group is attached to the 5-hydroxyl group by combining the unprotected F-28249 compound in an aprotic solvent such as methylene chloride, toluene, ethyl acetate, tetrahydrofuran, ethylenedichloride and the like, containing a tertiary amine, such as pyridine or triethylamine, and adding the protecting agent in the form of a acid halide. The reaction is conducted at a temperature of about 0° C. to 30° C. and is monitored by HPLC for completion.

The 23-hydroxyl group of the protected 13-deoxy-C-076-aglycone compound then is oxidized to the 23-oxo (or keto) group by using oxidizing agents such as pyridinium dichromate, pyridinium chlorochromate, chromic acid-dimethylpyrazole, acetic anhydride/dimethylsulfoxide, trifluoroacetic anhydride/dimethylsulfoxide, N-chlorosuccinimide/dimethylsulfoxide, oxalyl chloride/dimethylsulfoxide and the like. The reaction is carried out at dry-ice bath temperatures (about $-78°$ C.) to room temperature (about 25° C.) and is complete in about 1 to 24 hours, depending on the rate of oxidation, which is monitored by HPLC. The dimethylsulfoxide oxidation procedures are carried out in the presence of a tertiary amine such as triethylamine or diisopropylethylamine. Solvents such as methylene chloride, ethylenedichloride, dimethylformamide, dimethylsulfoxide and the like are used. In using oxalyl chloride/dimethylsulfoxide in the presence of triethylamine, it is advantageous to add molecular sieves to the reaction mixture to increase the yield. The oxidation may also be carried out by soil 5 microorganisms using 100 mg to 10 g of a 23-hydroxy compound per liter of unsterilized soil at 20° C. to 30° C. The oxidized 23-keto compound is extracted from the soil by a solvent such as acetone, methanol or ethanol.

The silyl protecting group is removed by stirring a protected 23-deoxy-C-076 compound in a lower alkanol such as methanol at 0° to room temperature for about 0.5 hour to an hour in the presence of an acid such as p-toluenesulfonic acid. If the protecting group is a silyloxyacetyl group, the silyl group is removed with acid as described above, and the hydroxyacetyl group is cleaved with an equivalent of base such as sodium methoxide in methanol at 0° to room temperature in 0.5 hour to several hours. The silyloxyacetyl group may also be removed in one step by treatment with sodium methoxide at room temperature until the reaction is complete. Similarly, other acyl protecting groups are removed by base treatment.

The imino derivatives of the 23-oxo compounds are readily prepared by standard techniques such as procedures described by S. M. McElvain in *The Characterization of Organic Compounds*, published by MacMillan Company, New York, 1953, pages 204–205 and incorporated herein by reference.

Typically, a 23-oxo compound is stirred in alcohol, such as methanol or ethanol, or dioxane in the presence of acetic acid and an excess of the amino derivatizing agent, such as hydroxylamine hydrochloride, O-methylhydroxylamine hydrochloride, semicarbazide hydrochloride and the like along with an equivalent amount of sodium acetate, at room temperature to 50° C. The reaction is usually complete in several hours to several days at room temperature but can be readily speeded by heating.

The O-acyloximes or carbamoylated oximes are prepared by treating the oximes of structure with acid anhydrides or isocyanates to afford (I), wherein $R_3$ is $C_1$–$C_6$ alkanoyl, chloroacetyl, methoxyacetyl, phenylacetyl, benzoyl, chlorobenzoyl, N-($C_1$–$C_4$ alkyl)carbamoyl, N-(allyl)carbamoyl, N-(propargyl)-carbamoyl, N-(phenyl)carbamoyl, N-(chlorophenyl)carbamoyl, N-dichlorophenyl)carbamoyl or N-benzyl)carbamoyl. The reactions are conducted in inert solvents, such as methylene chloride, ethylenedichloride or dioxane, in the presence of a tertiary amine, such as triethylamine or diisopropylethylamine. Generally, the reactions are conducted from 0° C. to room temperature, but if the reactions are sluggish, heat is applied. An equivalent to a slight excess of the acid anhydride is used to avoid reaction at the 5-hydroxy group.

The novel compounds of the present invention have significant activity as anthelmintics, ectoparasiticides, insecticides, nematicides and acaricides in human and animal health areas and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oestophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Paracaris. Certian of these, such as Nematodirus, Cooperia, and Oesphagostomum primarily attack the intestinal tract while others, such as Haemonchus and Ostertagia, are most prevalent in the stomach. Still others such as Dictyocaulus are found in the lungs. Also, other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs, and if left untreated, may result in death of the infected host. The 23-oxo or -imino derivatives of 13-deoxy-C-076 aglycone compounds of this invention unexpectedly have high activity against these parasites. Additionally, they also are active against Dirofilaria in dogs, Nematospiroides, Syphacia, Aspiculuris in rodents, arthropod ectoparasites such as ticks, mites, lice, fleas, blowfly of animals and birds, the ectoparasite Lucilia sp. of sheep, biting insects and migrating dipterous larvae such as Hypoderma sp. in cattle, Gastrophilus in horses and Cuterebra sp. in rodents.

The compounds of the present invention also are useful in treating, preventing or controlling parasites which infect human beings, as well. The most common genera of parasites of the gastrointestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra-intestinal stages of the intestinal worms Strongyloides and Trichinella. The present compounds also are of value against arthropods parasitizing man, biting insects and other dipterous pests causing annoyance to man.

These compounds further are active against household pests such as the cockroach, Blattella sp., clothes moth, Tineola sp., carpet beetle, Attagenus sp., and the housefly Musca domestica.

Insect pests of stored grains such as Tribolium sp., Tenebrio sp., and of agricultural plants such as spider mites (Tetranycus sp.), southern army worms, tobacco budworms, boll weevils, aphids (Acyrthiosiphon sp.), migratory orthopterans such as locusts and immature stages of insects living on plant tissue are controlled by the present compounds as well as the control of soil nematodes and plant parasites such as Meloidogyne sp., which may be of importance in agriculture.

The compounds of the present invention may be administered orally or parenterally for animal and human usage, while they may be formulated in liquid or solid form for agricultural use. Oral administration may take the form of a unit dosage form such as a capsule, bolus or tablet, or as a liquid drench where used as an anthelmintic for animals.

The animal drench is normally a solution, suspension or dispersion of the active compound, usually in water, together with a suspending agent such as bentonite and a wetting agent or like excipient. Generally, the drenches also contain an antifoaming agent. Drench formulations generally contain about 0.001% to 0.5%, by weight, of the active compound. Preferred drench formulations contain about 0.01% to 0.1% by weight.

Capsules and boluses comprise the active ingredient admixed with a carrier vehicle such as starch, talc, magnesium stearate or di-calcium phosphate.

Where it is desired to administer the 23-oxo or 23-imino derivatives of 13-deoxy-C-076 aglycone in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the active compound depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the active compounds of the present invention may be administered to animals parenterally, such as by intraruminal, intramuscular, intratracheal, or subcutaneous injection. In such an event, the active compound is dissolved or dispersed in a liquid carrier vehicle.

For parenteral administration, the active compound is suitable admixed with an acceptable vehicle, preferably of the vegetable oil variety such as peanut oil, cotton seed oil and the like. Other parenteral vehicles such as organic preparations using solketal, propylene glycol, glycerol formal, and aqueous parenteral formulation also are used. The active 23-oxo or -imino compound or compounds of the present invention are dissolved or suspended in the parenteral formulation for administration. Such formulations generally contain about 0.005% to 5%, by weight, of the active compound.

Although the compounds of the present invention are primarily uses in the treatment, prevention or control of helminthiasis, they also are useful in the prevention and treatment of diseases caused by other parasites. For example, arthropod parasites such as ticks, lice, fleas, mites and other biting insects in domesticated animals and poultry are controlled by the present compounds. These compounds also are effective in treatment of parasitic diseases that occur in other animals including human beings. The optimum amount to be employed will, of course, depend upon the particular compound employed, the species of animal to be treated and the type and severity of parasitic infection or infestation. Generally, the amount useful in oral administration of these novel compounds is about 0.001 mg to 10 mg per kg of animal body weight, such total dose being given at one time or in divided doses over a relatively short period of time (1–5 days). The preferred compounds of the invention give excellent control of such parasites in animals by administering about 0.025 mg to 3 mg per kg of animal body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the animal's feed, or dissolved or suspended in the drinking water, compositions are provided in which the active compound or compounds are intimately dispersed in an inert carrier or diluent. An inert carrier is one that will not react with the active component and that will be administered safely to animals. Preferably, a carrier for feed administration is one that is, or may be, an ingredient of the animal ration.

Suitable compositions include feed premixes or supplements in which the active compound is present in relatively large amounts, wherein said feed premixes or supplements are suitable for direct feeding to the animal or for addition to the feed either directly or after an intermediate dilution or blending step.

Typical carriers or diluents suitable for such compositions include distillers' dried grains, corn meal, citrus meal, fermentation residues, ground oyster shells, wheat shorts, molasses solubles, corn cob meal, edible bean mill feed, soya grints, crushed limestone and the like. The active compounds are intimately dispersed throughout the carrier by methods such as grinding, stirring, milling or tumbling. Compositions containing about 0.005% to 2.0%, by weight, of the active compound are particularly suitable as feed premixes.

Feed supplements, which are fed directly to the animal, contain about 0.0002% to 0.3%, by weight, of the active compounds. Such supplements are added to the animal feed in an amount to give the finished feed the concentration of active compound desired for the treatment, prevention and/or control of parasitic diseases. Although the desired concentration of active compound will vary depending upon the factors previously mentioned as well as upon the particular derivative employed, the compounds of this invention are usually fed at concentrations of about 0.00001% to 0.02% in the feed in order to achieve the desired antiparasitic result.

The compounds also may be administered by pouring on the skin of animals via a solution. Generally, the active compounds are dissolved in a suitable inert solvent, such as dimethylsulfoxide, propylene glycol of the like, alternatively in combination of solvents, for the pour-on administration.

The compounds of this invention also are useful in combating agricultural pests that inflict damage upon growing or stored crops. The present compounds are applied, using known techniques such as sprays, dusts, emulsions and the like, to the growing or stored crops to effect protection from such agricultural pests.

The present invention is illustrated by the following examples which are illustrative of said invention and not limitative thereof.

EXAMPLES 1–3

13-Deoxy-23-oxo-C-076-B2a-aglycone

A solution containing 0.32 g of oxalyl chloride in 5 mL of $CH_2Cl_2$ is cooled and stirred with 0.71 g of Type 4A molecular sieves in a dry-ice/acetone bath. A mixture of 0.4 g of dimethylsulfoxide (DMSO) in 2 mL of $CH_2Cl_2$ is added slowly with stirring under $N_2$ atmosphere. Subsequently, 0.83 g of 5-O-t-butyldimethylsilyl-13-deoxy-C-076-B2a-aglycone in 8 mL of $CH_2Cl_2$ is added dropwise over 10 minutes. After 0.5 hours, 1.6 mL of triethylamine is added dropwise, and the mixture's temperature is allowed to rise to room temperature over an hour. The mixture is poured on ice-$H_2O$ mixture, and the aqueous mixture is extracted with $3 \times 10$ mL of $Et_2IO$. The $Et_2O$ layers are washed with $H_2O$ ($5 \times 5$ mL) and dried ($M_9SO_4$). Ether is removed, and the residue is dissolved in 15 mL of MeOH. The MeOH solution is stirred at 0° C. with 0.3 g of p-toluenesulfonic acid for 3 hours and poured into 60 mL of saturated $NaHCO_3$ and 60 mL of $H_2O$. The aqueous mixture is stirred with NaCl until it is saturated and extracted with EtOAc ($3 \times 40$ mL). The combined EtOAc layers are dried ($M_9SO_4$) and evaporated to dryness to afford the title compound that is identified by mass spectrometry and NMR spectroscopy.

Similarly 5-O-t-butyldimethylsilyl-13-deoxy-23-oxo-C-076-B2b-aglycone is obtained from its corresponding alcohol. It is desilylated. Also, the oxidation of 5-O-t-butyldimethylsilyl-13-chloro-13-deoxy-C076-B2a-aglycone affords 13-chloro-13-deoxy-23-oxo-C-076-B2a-aglycone.

EXAMPLE 4

13-Deoxy-23-oxo-C-076-A2a-aglycone

Using the procedure of Examples 1 to 3, 5-O-t-butyl-dimethylsilyl-13-deoxy C-076-A2a-aglycone is oxidized to give the title compound that is identified by mass spectrometry and NMR spectroscopy.

EXAMPLE 5

13-Deoxy-23-O-Methyloxime-C-076-B2a-aglycone

In 9 mL of dry dioxane at room temperature, 0.70 g of 23-oxo-C-076-B2a-aglycone, 0.12 g of NaOAc, 0.12 g of $CH_3ONH_2 \cdot HCl$ and 0.02 mL of HOAc are added. The mixture is stirred under $N_2$ for 3 days, and after no starting material is detected by HPLC, dioxane is evaporated in vacuo. The residue is poured into 50 mL of $H_2O$, and the product is extracted with $CH_2Cl_2$ ($4 \times 20$ mL). The combined extracts are washed with $H_2O$, dried ($Na_2SO_4$) and evaporated to dryness. The residue is dissolved in 15 mL of $Et_2O$, and the solution is washed with $H_2O$, dried ($Na_2SO_4$) and evaporated to dryness to give the title compound that is identified by mass spectrometry and NMR spectroscopy.

EXAMPLE 6

13-Deoxy-23-oxime-C-076-B2a-aglycone

In 5 mL of dioxane, 62 mg of 13-deoxy-23-oxo-C-076-B2a-aglycone is stirred with 49 mg of $NH_2OH \cdot HCl$, 58 mg of NaOAc and 10 $\mu l$ of HOAc for 23 hours under $N_2$ atmosphere. The mixture is poured into 250 mL each of $H_2O$ and $CH_2Cl_2$, and the $CH_2Cl_2$ layer is separated. The aqueous layer is extracted with 50 mL of $CH_2Cl_2$, and the combined $CH_2Cl_2$ solutions are washed with $H_2O$, dried ($Na_2SO_4$) and evaporated to dryness to afford 8.8 mg of residue. This material is purified on a preparative layer plate (silica gel) using 20% MeOH in $CH_2Cl_2$ to afford the title compound that is identified by mass spectrometry and NMR spectroscopy.

EXAMPLE 7

13-Deoxy-23-[O-(methylcarbamoyl)oxime]-C-076-B2a-aglycone

In 5 mL of $Et_2O$, 27.2 mg of 13-deoxy-23-oxo-C-076-B2a-aglycone is stirred under $N_2$ with 10 $\mu l$ of $Et_3N$ and 50 $\mu L$ of methyl isocyanate for 17 hours at room temperature. The ether is evaporated, and the residue is purified on a preparative chromatography plate (silica gel) using 20% MeOH in $CH_2Cl_2$ to afford the title compound that is identified by mass spectrometry and NMR spectroscopy.

EXAMPLES 8–17

Using the method of Example 4, the following 13-deoxy-23-0-substituted oxime-C-076-B2-aglycone compounds are prepared using the appropriate O-substituted hydroxylamines in place of methoxyamine.

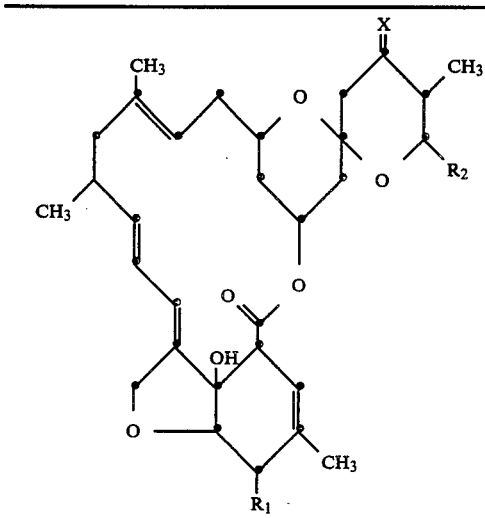

| R₁ | R₂ | X |
|---|---|---|
| OH | sec-butyl | N—O—ethyl |
| OCH₃ | isopropyl | N—O—ethyl |
| OH | sec-butyl | N—O—isopropyl |
| OH | sec-butyl | N—O—n-hexyl |
| OH | sec-butyl | N—O—benzyl |
| OH | sec-butyl | N—O—allyl |
| OH | sec-butyl | N—O—propargyl |
| OH | sec-butyl | N—O—CH₂COOC₂H₅ |
| OH | sec-butyl | N—OCH₂COOC₄H₉ |
| OCH₃ | sec-butyl | N—O—ethyl |

EXAMPLES 18–27

Using the method of Example 7, the following 23-(O-substituted-carbamoyl)oximes are prepared:

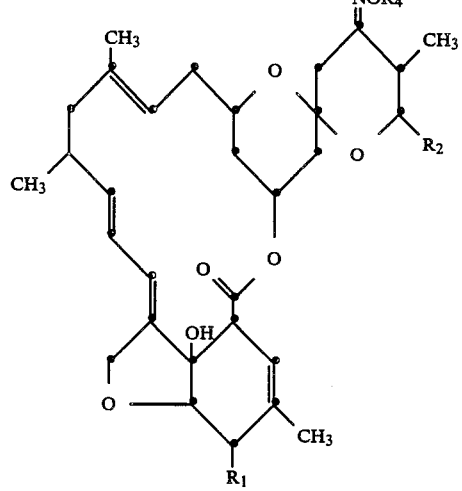

| R₁ | R₂ | R₄ |
|---|---|---|
| OH | sec-butyl | i-C₃H₇NHCO |
| OH | isopropyl | i-C₃H₇NHCO |
| OH | sec-butyl | C₂H₅NHCO |
| OCH₃ | sec-butyl | C₂H₅NHCO |
| OH | sec-butyl | phenyl-NHCO |
| OH | sec-butyl | allyl-NHCO |
| OH | sec-butyl | propargyl-NHCO |
| OH | sec-butyl | 4-chlorophenyl-NHCO |
| OH | sec-butyl | 3,4-dichlorophenyl-NHCO |

-continued

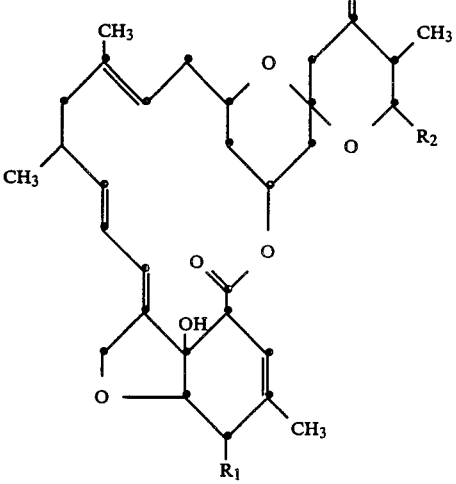

| R₁ | R₂ | R₄ |
|---|---|---|
| OH | sec-butyl | benzyl-NHCO |

EXAMPLE 28

13-Deoxy-23-[O-acetyl)oxime]-C-076-B2a-aglycone

In 1 mL of CH₂Cl₂, 50 mg of 13-deoxy-23-oxime-C-076-B2a aglycone is stirred at 0° C. with 6 μL of triethylamine and 1.25 equivalents of acetic anhydride for hours. The mixture is evaporated to dryness, and the residue is dissolved in 10 mL of CH₂Cl₂. The CH₂Cl₂ solution is washed with H₂O, dried over M₉SO₄ and evaporated to dryness to afford the title compound that is identified by mass spectrometry and NMR spectroscopy.

EXAMPLES 29–33

By the procedure of Example 28, the following 13-deoxy-23-[O-(substituted)oxime]C-076-B2a aglycones are prepared using the appropriate acid anhydride.

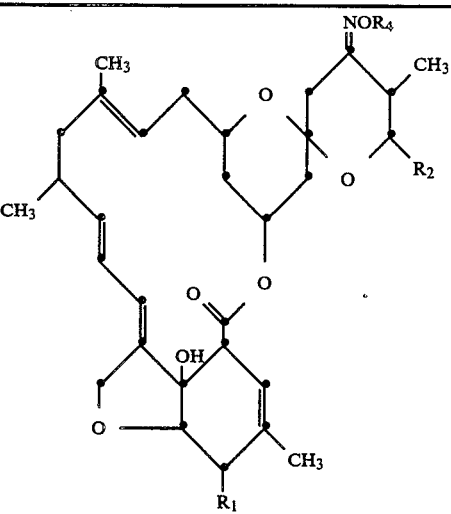

| R₁ | R₂ | R₄ |
|---|---|---|
| OH | sec-butyl | ClCH₂CO |
| OCH₃ | sec-butyl | ClCH₂CO |

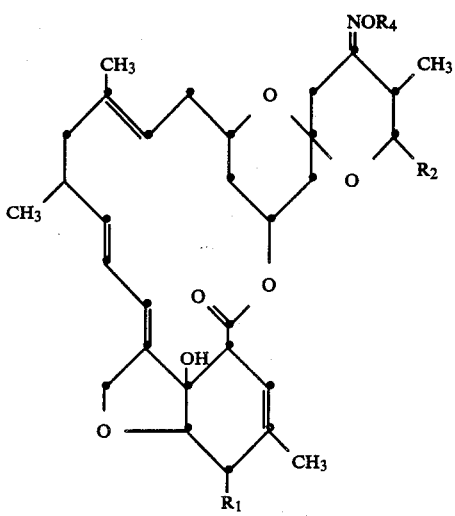

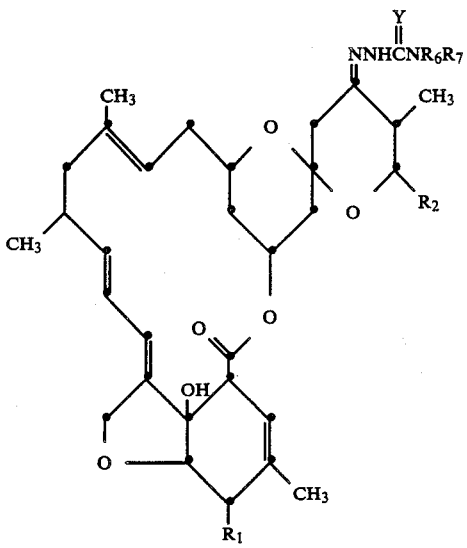

| R₁ | R₂ | R₄ |
|---|---|---|
| OH | sec-butyl | $CH_3OCH_2CO$ |
| OH | isopropyl | $CH_3OCH_2CO$ |
| OH | sec-butyl | $C_6H_5CH_2CO$ |

| R₁ | R₂ | Y | R₆ | R₇ |
|---|---|---|---|---|
| $OCH_3$ | sec-butyl | O | H | H |
| OH | sec-butyl | S | H | H |
| OH | isopropyl | O | H | H |
| OH | sec-butyl | O | H | $CH_3$ |
| OH | sec-butyl | O | H | $n-C_4H_9$ |
| OH | sec-butyl | O | $CH_3$ | $CH_2$ |
| OH | sec-butyl | S | $CH_3$ | H |
| OH | sec-butyl | S | H | $C_6H_5$ |
| OH | isopropyl | O | H | $C_6H_5$ |

EXAMPLE 34

13-Deoxy-23-semicarbazone-C-076-B2a aglycone

In 5 mL of dioxane, 60 mg of 13-deoxy-23-oxo-C-076-B2a-aglycone is stirred with 56.4 mg of NaOAc, mg of semicarbazide hydrochloride and 18 L of HOAc, for 6 days at room temperature. The mixture is poured on ice, mixed with 100 mL each of $H_2O$ and $CH_2Cl_2$. The $CH_2Cl_2$ layer is separated. The aqueous is extracted with $CH_2Cl_2$, and the combined $CH_2Cl_2$ solutions are washed with $H_2O$ and evaporated to dryness. The residue is dissolved in 100 mL of $Et_2O$ and the solution is washed with 8×50 mL of water, dried ($Na_2SO_4$) and evaporated to dryness to afford the title compound.

EXAMPLES 35–41

Using the procedure of Example 34, the following semicarbazones and thiosemicarbazones are prepared:

EXAMPLES 42–45

13-Deoxy-23-(2-carbomethoxyhydrazone)-C-076-B2a-aglycone

In 15 ml of MeOH, 50 mg of 13-deoxy-23-oxo-C-076-B2a-aglycone is treated with 25 mg of methyl carbazate and 10 μL of HOAc. After 3 days, the mixture is poured on ice and diluted with $H_2O$. The aqueous phase is saturated with NaCl and extracted with $CH_2Cl_2$. The $CH_2Cl_2$ extracts are dried ($Na_2SO_4$) and evaporated to dryness. The residue is purified by chromatography on silica gel using 2% isopropanol in $CH_2Cl_2$ to afford the title compound.

Similarly, the 2-carbethoxyhydrazone, 2-carbopropoxy and 2-carbobutoxy hydrazones are prepared using the corresponding carbazates.

What is claimed is:

1. A compound represented by structural formula (I):

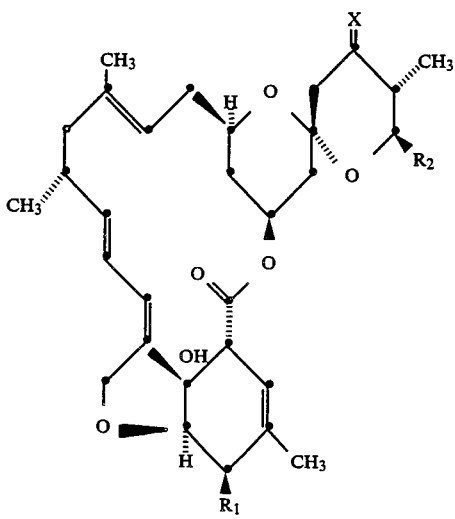

(I)

wherein R₁ is methoxy or hydroxy; R₂ is isopropyl or sec-butyl; X is NOR₄, or N-NHR₅; R₄ is hydrogen, $C_1$-$C_6$alkyl, $C_1$-$C_4$alkoxymethyl, benzyl, allyl, propargyl, phenyl, CH₂COO-alkyl ($C_1$-$C_4$), N-($C_1$-$C_6$ alkkyl)-carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1$-$C_6$ alkanoyl, chloroacetyl, methoxyacetyl, phenylacetyl, optionally substituted on the phenyl ring with one or two halogens, $C_1$-$C_4$ alkyl groups, $C_1$-$C_4$ alkoxy groups or nitro groups, phenoxyacetyl, optionally substituted on the phenyl ring by one or two halogens, $C_1$-$C_4$ alkyl groups, $C_1$-$C_4$ alkoxy groups or nitro groups, or benzoyl, optionally substituted with one or two halogens, $C_1$-$C_4$ alkyl groups, $C_1$-$C_4$ alkoxy groups or nitro groups; R₅ is

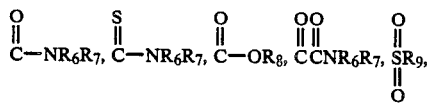

$C_1$-$C_6$ alkanoyl, $C_1$-$C_6$ alkyl,

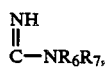

or benzoyl, optionally substituted with one or two halogens, $C_1$-$C_4$ alkyl groups, $C_1$-$C_4$ alkoxy groups or nitro groups; R₆ and R₇ are hydrogen or $C_1$-$C_6$ alkyl; or phenyl, optionally substituted with one or two halogens, $C_1$-$C_4$ alkyl, $C_1$-$C_4$ alkoxy, or phenyl optionally substituted with one or two halogens $C_1$-$C_4$ alkyl groups, $C_1$-$C_4$ alkoxy groups or nitro groups, R₈ is $C_1$-$C_6$ alkyl or phenyl optionally substituted with one or two halogens, $C_1$-$C_4$ alkyl groups, $C_1$-$C_4$ alkoxy groups or nitro groups; R₉ is $C_1$-$C_6$ alkyl or phenyl optionally substituted with one or two halogens, $C_1$-$C_4$ alkyl groups, $C_1$-$C_4$ alkoxy groups or nitro groups; or a pharmaceutically and pharmacologically acceptable salt thereof.

2. The compound according to claim 1, wherein R₁ is hydroxy; R₂ is isopropyl or sec-butyl; X is

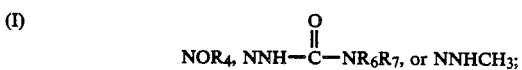

R₄ is $C_1$-$C_3$ alkyl, N-($C_1$-$C_4$ alkyl)carbamoyl, N-(phenyl)carbamoyl, N-(4-chlorophenyl)carbamoyl, N-(allyl)carbamoyl, N-(benzyl)carbamoyl, $C_1$-$C_4$ alkanoyl, chloroacetyl, methoxyacetyl, benzoyl or chlorobenzoyl and R₆ and R₇ are as described in said claim 1.

3. The compound according to claim 1, wherein R₁ is hydroxy; R₂ is isopropyl or sec-butyl; X is

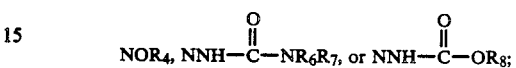

and R₄, R₆, R₇ and R₈ are as described in said claim 1.

4. The compound according to claim 1, wherein R₁ is hydroxy; R₂ is sec-butyl; and X is NOCH₃.

5. The compound according to claim 1, wherein R₁ is hydroxy; R₂ is sec-butyl; and X is

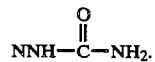

6. A method for the prevention, treatment or control of endoparasitic or ectoparasitic infections in warm-blooded animals, said method comprising: orally, topically or parenterally administering to an animal infected with endoor ectoparasites, an endo- or ectoparasiticidally effective amount of a compound represented by structural formula (I),

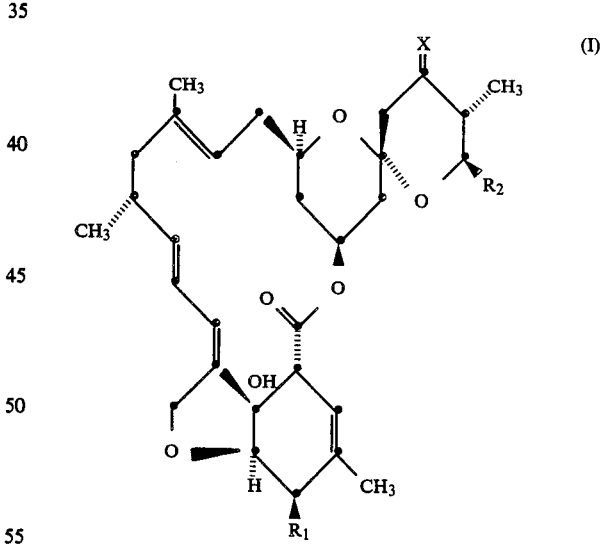

(I)

wherein R₁ is methoxy or hydroxy; R₂ is isopropyl or sec-butyl; X is NOR₄, or N-NHR₅; R₄ is hydrogen, $C_1$-$C_6$alkyl, $C_1$-$C_4$alkoxymethyl, benzyl, allyl, propargyl, phenyl, CH₂COO-alkyl ($C_1$-$C_4$), N-($C_1$-$C_6$ alkyl)-carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1$-$C_6$ alkanoyl, chloroacetyl, methoxyacetyl, phenylacetyl, optionally substituted on the phenyl ring with one or two halogens, $C_1$-$C_4$ alkyl groups, $C_1$-$C_4$ alkoxy groups or nitro groups, phenoxyacetyl, optionally substituted on the phenyl ring by one or two halogens, $C_1$-$C_4$ alkyl groups, $C_1$-$C_4$ alkoxy groups or nitro groups, or benzoyl, optionally substituted with one or two halogens, $C_1$-$C_4$ alkyl groups, $C_1$-$C_4$ alkoxy groups or nitro groups; $R_5$ is

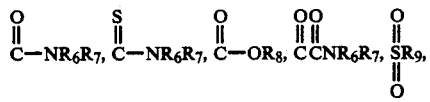

$C_1$-$C_6$ alkanoyl, $C_1$-$C_6$ alkyl,

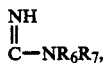

or benzoyl, optionally substituted with one or two halogens, $C_1$-$C_4$ alkyl groups, $C_1$-$C_4$ alkoxy groups or nitro groups; $R_6$ and $R_7$ are hydrogen or $C_1$-$C_6$ alkyl; or phenyl, optionally substituted with one or two halogens, $C_1$-$C_4$ alkyl, $C_1$-$C_4$ alkoxy, or phenyl optionally substituted with one or two halogens, $C_1$-$C_4$ alkyl groups, $C_1$-$C_4$ alkoxy groups or nitro groups, $R_8$ is $C_1$-$C_6$ alkyl or phenyl optionally substituted with one or two halogens, $C_1$-$C_4$ alkyl groups, $C_1$-$C_4$ alkoxy groups or nitro groups; $R_9$ is $C_1$-$C_6$ alkyl or phenyl optionally substituted with one or two halogens, $C_1$-$C_4$ alkyl groups, $C_1$-$C_4$ alkoxy groups or nitro groups; or a pharmaceutically and pharmacologically acceptable salt thereof.

7. A method according to claim 6, wherein said compound has $R_1$ as hydroxy; $R_2$ is sec-butyl; and X is $NOCH_3$.

8. A method according to claim 6, wherein said compound has $R_1$ as hydroxy; $R_2$ is sec-butyl; and X is

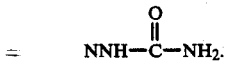

9. A method for protecting crops, trees, shrubs, stored grain and ornamentals from attack by acarids or insects which infest them, said method comprising: applying an acaricidally or insecticidally-effective amount of a compound represented by structural formula (I),

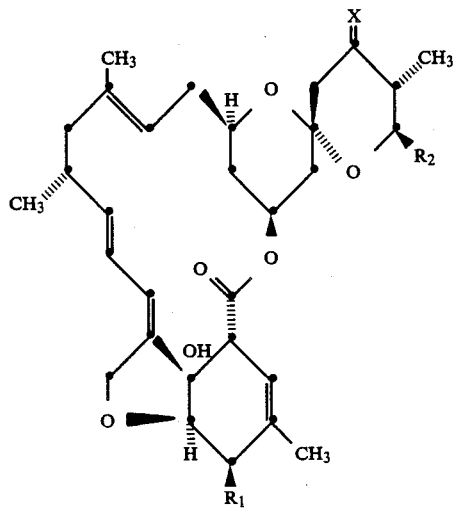

wherein $R_1$ is methoxy or hydroxy; $R_2$ is isopropyl or sec-butyl; X is $NOR_4$, or $N$-$NHR_5$; $R_4$ is hydrogen, $C_1$-$C_6$alkyl, $C_1$-$C_4$alkoxymethyl, benzyl, allyl, propargyl, phenyl, $CH_2COO$-alkyl ($C_1$-$C_4$), N-($C_1$-$C_6$ alkyl)-carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1$-$C_6$ alkanoyl, chloroacetyl, methoxyacetyl, phenylacetyl, optionally substituted on the phenyl ring with one or two halogens, $C_1$-$C_4$ alkyl groups, $C_1$-$C_4$ alkoxy groups or nitro groups, phenoxyacetyl, optionally substituted on the phenyl ring by one or two halogens, $C_1$-$C_4$ alkyl groups, $C_1$-$C_4$ alkoxy groups or nitro groups, or benzoyl, optionally substituted with one or two halogens, $C_1$-$C_4$ alkyl groups, $C_1$-$C_4$ alkoxy groups or nitro groups; $R_5$ is

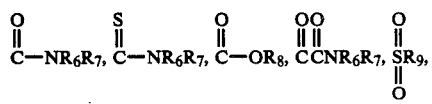

$C_1$-$C_6$ alkanoyl, $C_1$-$C_6$ alkyl,

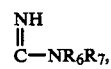

or benzoyl, optionally substituted with one or two halogens, $C_1$-$C_4$ alkyl groups, $C_1$-$C_4$ alkoxy groups or nitro groups; $R_6$ and $R_7$ are hydrogen or $C_1$-$C_6$ alkyl; or phenyl, optionally substituted with one or two halogens, $C_1$-$C_4$ alkyl, $C_1$-$C_4$ alkoxy, or phenyl optionally substituted with one or two halogens, $C_1$-$C_4$ alkyl groups, $C_1$-$C_4$ alkoxy groups or nitro groups, $R_8$ is $C_1$-$C_6$ alkyl or phenyl optionally substituted with one or two halogens, $C_1$-$C_4$ alkyl groups, $C_1$-$C_4$ alkoxy groups or nitro groups; $R_9$ is $C_1$-$C_6$ alkyl or phenyl optionally substituted with one or two halogens, $C_1$-$C_4$ alkyl groups, $C_1$-$C_4$ alkoxy groups or nitro groups; or a pharmaceutically and pharmacologically acceptable salt thereof.

10. A method according to claim 9, wherein said compound has $R_1$ as hydroxy; $R_2$ is sec-butyl; and X is $NOCH_3$.

11. A method for the control of plant nematodes, said method comprising: applying to the foliage of plants, the soil in which they are grown or into the trunks thereof, a nematocidally-effective amount of a compound represented by structural formula (I),

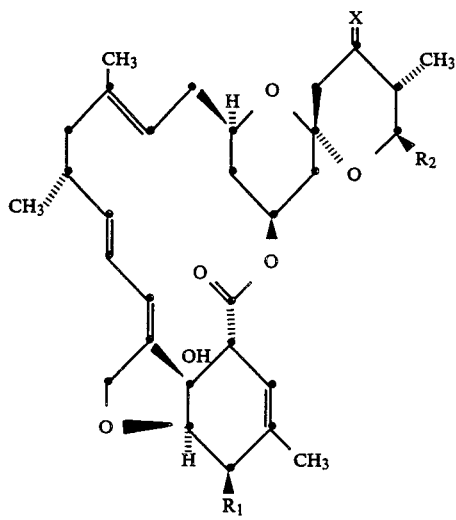

wherein $R_1$ is methoxy or hydroxy; $R_2$ is isopropyl or sec-butyl; X is $NOR_4$, or $N-NHR_5$; $R_4$ is hydrogen, $C_1-C_6$alkyl, $C_1-C_4$alkoxymethyl, benzyl, allyl, propargyl, phenyl, $CH_2COO$-alkyl ($C_1-C_4$), N-($C_1-C_6$ alkyl)-carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1-C_6$ alkanoyl, chloroacetyl, methoxyacetyl, phenylacetyl, optionally substituted on the phenyl ring with one or two halogens, $C_1-C_4$ alkyl groups, $C_1-C_4$ alkoxy groups or nitro groups, phenoxyacetyl, optionally substituted on the phenyl ring by one or two halogens, $C_1-C_4$ alkyl groups, $C_1-C_4$ alkoxy groups or nitro groups, or benzoyl, optionally substituted with one or two halogens, $C_1-C_4$ alkyl groups, $C_1-C_4$ alkoxy groups or nitro groups; $R_5$ is

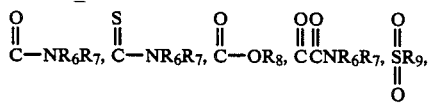

$C_1-C_6$ alkanoyl, $C_1-C_6$ alkyl,

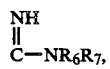

or benzoyl, optionally substituted with one or two halogens, $C_1-C_4$ alkyl groups, $C_1-C_4$ alkoxy groups or nitro groups; $R_6$ and $R_7$ are hydrogen or $C_1-C_6$ alkyl; or phenyl, optionally substituted with one or two halogens, $C_1-C_4$ alkyl, $C_1-C_4$ alkoxy, or phenyl optionally substituted with one or two halogens, $C_1-C_4$ alkyl groups, $C_1-C_4$ alkoxy groups or nitro groups, $R_8$ is $C_1-C_6$ alkyl or phenyl optionally substituted with one or two halogens, $C_1-C_4$ alkyl groups, $C_1-C_4$ alkoxy groups or nitro groups; $R_9$ is $C_1-C_6$ alkyl or phenyl optionally substituted with one or two halogens, $C_1-C_4$ alkyl groups, $C_1-C_4$ alkoxy groups or nitro groups; or a pharmaceutically and pharmacologically acceptable salt thereof.

12. A method according to claim 11, wherein said compound has $R_1$ as hydroxy; $R_2$ is sec-butyl; and X is $NOCH_3$.

13. A composition for treating, preventing or controlling endo- or ectoparasitic infections in warm-blooded animals or for controlling insects, said composition comprising: a pharmacologically or insecticidally-effective amount of a compound represented by structural formula (I),

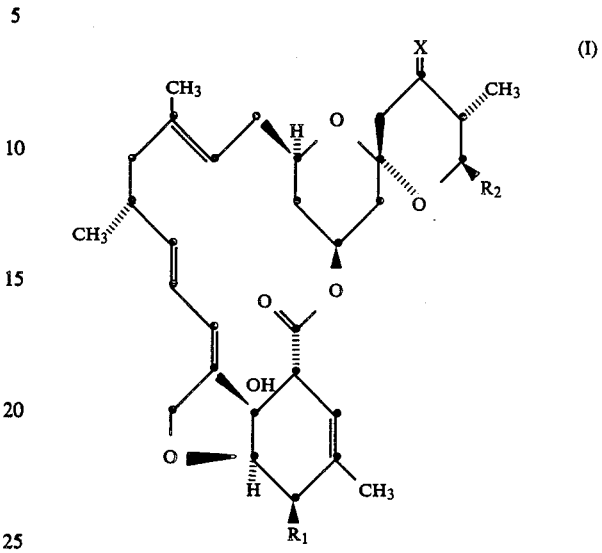

wherein $R_1$ is methoxy or hydroxy; $R_2$ is isopropyl or sec-butyl; X is $NOR_4$, or $-NHR_5$; $R_4$ is hydrogen, $C_1-C_6$ alkyl, $C_1-C_4$alkoxymethyl, benzyl, allyl, propargyl, phenyl, $CH_2COO$-alkyl ($C_1-C_4$), N-($C_1-C_6$ alkyl)-carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1-C_6$ alkanoyl, chloroacetyl, methoxyacetyl, phenylacetyl, optionally substituted on the phenyl ring with one or two halogens, $C_1-C_4$ alkyl groups, $C_1-C_4$ alkoxy groups or nitro groups, phenoxyacetyl, optionally substituted on the phenyl ring by one or two halogens, $C_1-C_4$ alkyl groups, $C_1-C_4$ alkoxy groups or nitro groups, or benzoyl, optionally substituted with one or two halogens, $C_1-C_4$ alkyl groups, $C_1-C_4$ alkoxy groups or nitro groups; $R_5$ is

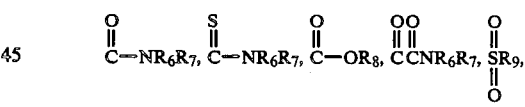

$C_1-C_6$ alkanoyl, $C_1-C_6$ alkyl,

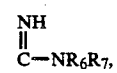

or benzoyl, optionally substituted with one or two halogens, $C_1-C_4$ alkyl groups, $C_1-C_4$ alkoxy groups or nitro groups; $R_6$ and $R_7$ are hydrogen or $C_1-C_6$ alkyl; or phenyl, optionally substituted with one or two halogens, $C_1-C_4$ alkyl, $C_1-C_4$ alkoxy, or phenyl optionally substituted with one or two halogens, $C_1-C_4$ alkyl groups, $C_1-C_4$ alkoxy groups or nitro groups, $R_8$ is $C_1-C_6$ alkyl or phenyl optionally substituted with one or two halogens, $C_1-C_4$ alkyl groups, $C_1-C_4$ alkoxy groups or nitro groups; $R_9$ is $C_1-C_6$ alkyl or phenyl optionally substituted with one or two halogens, $C_1-C_4$ alkyl groups, $C_1-C_4$ alkoxy groups or nitro groups; or a pharmaceutically and pharmacologically acceptable salt thereof and an inert carrier.

* * * * *

UNITED STATES PATENT AND TRADEMARK OFFICE
CERTIFICATE OF CORRECTION

PATENT NO. : 4,877,888                                Page 1 of 3
DATED      : October 31, 1989
INVENTOR(S): Goro Asato; Donald J. France It is certified that error appears in the above-identified patent and that said Letters Patent is hereby corrected as shown below:

In Column 1, lines 38-45, that portion of the formula reading 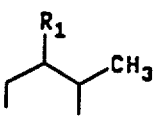 should read 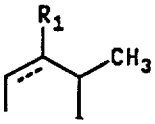. In Column 3, lines 1-8, that portion of the formula reading 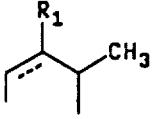 should read 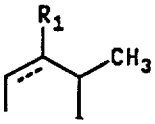.

In Column 5, line 6, "-butyldimethylsilyl" should read --$\underline{t}$-butyldimethylsilyl--. In Column 9, line 44, "$Et_2IO$" should read --$Et_2O$--. In Column 13, line 43, that portion at the end of the line reading ", mg of" should read --, 77 mg of--.

UNITED STATES PATENT AND TRADEMARK OFFICE
CERTIFICATE OF CORRECTION

PATENT NO. : 4,877,888

DATED : October 31, 1989

INVENTOR(S) : Goro Asato; Donald J. France

It is certified that error appears in the above-identified patent and that said Letters Patent is hereby corrected as shown below:

In claim 1, Column 15, line 26, that portion at the end of the line reading "N-($C_1$-$C_6$ alkkyl)-" should read --N-($C_1$-$C_6$ alkyl)- --; and, line 57, after the term halogens, a comma should appear.

In claim 6, Column 16, line 32, "endoor" should read --endo- or--.

In claim 13, Column 20, line 28, "-$NHR_5$" should read --N-$NHR_5$--.

UNITED STATES PATENT AND TRADEMARK OFFICE
CERTIFICATE OF CORRECTION

PATENT NO. : 4,877,888

DATED : October 31, 1989

INVENTOR(S) : Goro Asato; Donald J. France

It is certified that error appears in the above-identified patent and that said Letters Patent is hereby corrected as shown below:

In Column 9, line 16, "of" should read --or--; and, lines 45 and 52, "M$_9$SO$_4$" should read --MgSO$_4$--. In Column 12, line 35, "M$_9$SO$_4$" should read --MgSO$_4$--. In Column 13, line 45, "18 L" should read --18 $\mu$L--.

Signed and Sealed this

Nineteenth Day of May, 1992

Attest:

DOUGLAS B. COMER

*Attesting Officer*   *Acting Commissioner of Patents and Trademarks*